United States Patent [19]

Roussel et al.

[11] Patent Number: 5,508,452
[45] Date of Patent: Apr. 16, 1996

[54] PREPARATION OF 16α-METHYL STEROIDS

[75] Inventors: Patrick Roussel, Thiais; Michel Vivat, Lagny sur Marne, both of France

[73] Assignee: Roussel Uclaf, France

[21] Appl. No.: 180,454

[22] Filed: Jan. 12, 1994

[30] Foreign Application Priority Data

Jan. 20, 1993 [FR] France .................................. 93 00519

[51] Int. Cl.[6] ........................................................ C07J 1/00
[52] U.S. Cl. ................................................................. 552/505
[58] Field of Search ..................................... 552/505

[56] References Cited

U.S. PATENT DOCUMENTS

| Re. 28,369 | 3/1975 | Arth et al. | 552/507 |
|---|---|---|---|
| 3,080,393 | 3/1963 | Stork et al. | 552/596 |
| 4,071,624 | 1/1978 | Grunwell | 552/505 |
| 4,704,455 | 11/1987 | Van Rheenen | 552/505 |
| 4,772,755 | 9/1988 | Liotta | 552/293 |
| 4,929,395 | 5/1990 | Van Rheenen | 552/505 |
| 4,990,612 | 2/1991 | Van Rheenen | 552/505 |
| 5,149,696 | 9/1992 | Claussner | 552/540 |

FOREIGN PATENT DOCUMENTS

| 0165037 | 12/1985 | European Pat. Off. |
|---|---|---|
| 2318647 | 2/1977 | France . |
| 1277266 | 6/1972 | United Kingdom . |
| WO87/07612 | 12/1987 | WIPO . |

OTHER PUBLICATIONS

Search Report No. 9300519 (for FR 9300519 21 Oct. 1993).
Fried, "Organic Reactions", Van Nostrand pp. 75–76 1972.

Primary Examiner—Gary E. Hollinden
Assistant Examiner—Catherine Kilby Scalzo
Attorney, Agent, or Firm—Bierman and Muserlian

[57] ABSTRACT

A process for the preparation of a compound of the formula

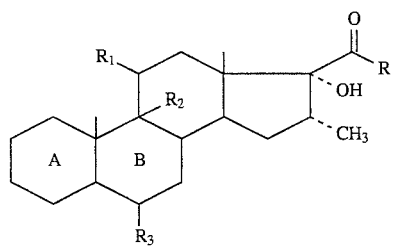

in which rings A and B are a remainder:

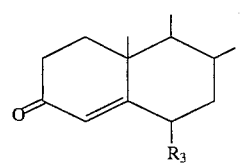

-continued

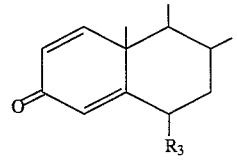

in which the 3-ketone function is optionally protected in the form of a ketal, thioketal, hemithioketal or enol ether, or a remainder:

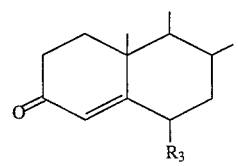

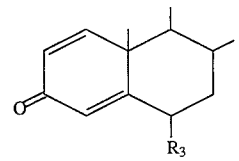

wherein R is methyl or —$CH_2$—OR', R' is hydrogen or ether remainder or ester remainder, $R_1$ and $R_2$ together form a second bond, or $R_1$ and $R_2$ form together an epoxide in beta position, or $R_1$ is hydrogen, ketone or α- or β- hydroxy, free or protected in the form of an ether or ester and $R_2$ is hydrogen, or $R_1$ is hydrogen and $R_2$ is α-hydroxy function, or $R_1$ is β-hydroxy, free or protected in the form of an ether or ester and $R_2$ is α-fluorine or bromine and $R_3$ is hydrogen or α or β fluorine or methyl comprising reacting a compound of the formula

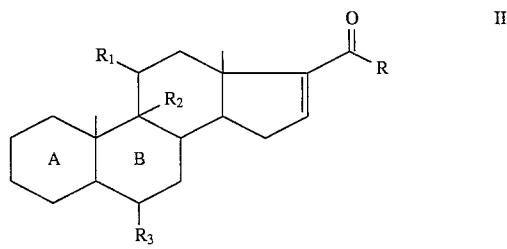

in which A, B, R, $R_1$, $R_2$ and $R_3$ have the above meaning with a methylation agent in the presence of a copper-based catalyst to form the 16α-methylated enolate, hydrolyzing the latter to obtain the corresponding enol and reacting the latter with an oxidizing agent to obtain the compound of formula I.

12 Claims, No Drawings

PREPARATION OF 16α-METHYL STEROIDS

STATE OF THE ART

WO application No. 87/07,612 describes the preparation of 16α-methyl steroids of formula I by methylating an 16-unsaturated steroid with a methylation agent in the presence of a copper-based catalyst and a silylation agent to form an intermediate enol ether of the formula

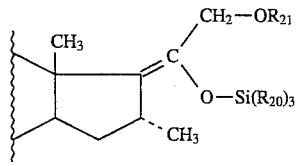

which is then treated with a peracid to form the 17α, 20 epoxide of the formula

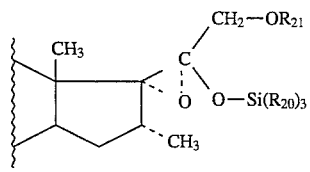

which is finally hydrolyzed with an acid or a base. This process therefore requires the passage of an epoxide originating from a stabilized enol in the form of the silylated ether which must then be hydrolyzed.

OBJECTS OF THE INVENTION

It is an object of the invention to provide a novel method for the preparation of 16α-methyl steroids passing through an enol in stabilized form and without a final hydrolysis step.

This and other objects and advantages of the invention will become obvious from the following detailed description.

THE INVENTION

The novel process of the invention for the preparation of the 16α-methyl steroids of the formula

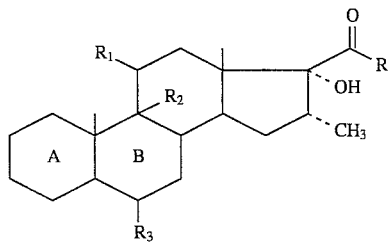

in which rings A and B are a remainder:

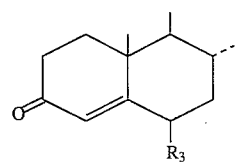

in which the 3-ketone function is optionally protected in the form of a ketal, thioketal, hemithioketal or enol ether, or a remainder:

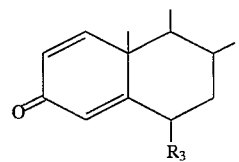

wherein R is methyl or —$CH_2$—OR', R' is hydrogen or ether remainder or ester remainder, $R_1$ and $R_2$ together form a second bond, or $R_1$ and $R_2$ form together an epoxide in beta position, or $R_1$ is hydrogen, ketone or α- or β- hydroxy, free or protected in the form of an ether or ester and $R_2$ is hydrogen, or $R_1$ is hydrogen and $R_2$ is α-hydroxy function, or $R_1$ is β-hydroxy, free or protected in the form of an ether or ester and $R_2$ is α-fluorine or bromine and $R_3$ is hydrogen or α or β fluorine or methyl comprises reacting a compound of the formula

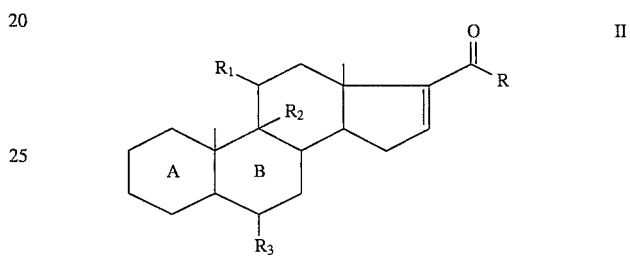

in which A, B, R, $R_1$, $R_2$ and $R_3$ have the above meaning with a methylation agent in the presence of a copper-based catalyst to form the 16α- methylated enolate, hydrolyzing the latter to obtain the corresponding enol and reacting the latter with an oxidizing agent to obtain the compound of formula I.

When the 3-ketone function is protected in the ketal, thioketal or hemithioketal form, it is preferably a group of the formula

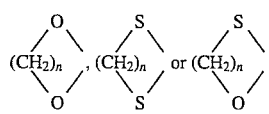

in which n is 2 or 3 and quite particularly an ethylenedioxy or ethylenedithio. When the 3-ketone function is protected in the enol ether form, it is preferably an alkoxy or alkoxyalkoxy of 1 to 8 carbon atoms and more particularly methoxy, ethoxy, ethoxyethoxy or 1-ethoxy-ethoxy, rings A and B then containing a system of Δ 3,5 double bonds.

When R' is an ether remainder, it can be any remainder known to one skilled in the art and preferably alkyl of 1 to 6 carbon atoms such as methyl, ethyl or propyl, tetrahydropyranyl or a silylated ether remainder such as trialkylsilyl such as trimethyl- or dimethylterbutylsilyl, triarylsilyl such as triphenylsilyl or diarylalkylsilyl such as diphenylterbutylsilyl.

When R' is an ester remainder, it can be any remainder known to one skilled in the art and preferably acyl of an organic carboxylic acid of 1 to 8 carbon atoms such as formyl, acetyl, propionyl, butyryl, valeryl or benzoyl.

When $R_1$ is a protected hydroxy in the form of an ether or ester, it can be one of the ether or ester remainders mentioned above for R', it being understood that these remainders are not necessarily identical.

A preferred process comprising using a compound of formula II as a starting material in which rings A and B are

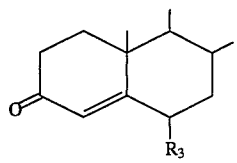

or

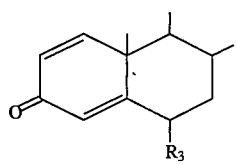

in which $R_3$ is defined as above and the 3-ketone function is free, the last being more particularly preferred.

Another preferred process comprises using as the starting compound of formula II a compound wherein $R_1$ and $R_2$ together form a second bond, or $R_1$ and $R_2$ form together a β-epoxide, or $R_1$ is β-hydroxy, free or protected in the form of an ether or ester and $R_2$ is α-fluorine, and $R_3$ is hydrogen, fluorine or methyl and, preferably, hydrogen.

The methylation agent used can be a methylated derivative of copper, for example $CH_3Cu$, $(CH_3)_2 CuMg$, $(CH_3)_2 CuLi$ or, preferably, a methyl magnesium chloride, bromide or iodide used in the presence of a copper-based catalyst. The catalyst can be a salt such as cupric acetate, propionate or chloride, cuprous chloride, bromide, iodide or cyanide, or also a complex, for example copper acetylacetonate, cuprous dimethylsulfide bromide or cuprous tri-n-butylphosphine chloride or any other complex of the same type known to one skilled in the art. Cupric acetate and propionate are particularly preferred.

The operation is carried out in a solvent which is preferably an ether such as tetrahydrofuran, ethyl ether, tert-butyl methyl ether, di-n-butyl ether. Tetrahydrofuran is particularly preferred. The operation is advantageously carried out at a temperature of 0° to –30° C. and, preferably, at –20° C.

The hydrolysis of the 16α-methylated enolate is preferably carried out under an inert gas atmosphere by pouring the reaction solution into an aqueous solution of a monoalkali metal phosphate, for example of sodium or potassium, or into a buffer of weakly acidic pH, notably a phosphate buffer, or, more generally into a weak acidic agent such as acetic acid, propionic acid or butyric acid, or also into an aqueous solution of ammonium chloride or acetate. A phosphate buffer is more particularly preferred.

The hydrolysis is preferably followed by an oxidizing treatment to convert the cuprous ions present in the mixture into cupric ions for the purpose of facilitating the precipitation. The standard oxidizing agents known to one skilled in the art for producing this conversion can be used. By way of example, it can be indicated that hydrogen peroxide is particularly suitable. The precipitation is made even easier by the addition of an alkali metal salt, for example sodium sulfate or chloride, to saturate the medium.

The oxidation of the enol can be carried out by a standard oxidizing agent such as hydrogen peroxide, used alone or combined either with a transition metal, preferably titanium, manganese or tungsten, or with acetone or a derivative, notably hexachloro or hexafluoro acetone, or potassium permanganate, activated or not by metals such as copper, or by an agent more particularly for epoxidation such as a dioxirane, for example dimethyldioxirane, a hydroperoxide, for example terbutyl hydroperoxide, or a peracid, for example perphthalic acid, perbenzoic acid, n-chloroperbenzoic acid, peracetic acid, trifluoroperacetic acid or permaleic acid. Oxidation by a peracid is particularly preferred.

The operation is preferably carried out under an inert gas atmosphere in a halogenated solvent such as methylene chloride, chloroform, dichloroethane, or an ether such as ethyl ether, tetrahydrofuran or dioxane, or an aromatic solvent such as toluene, or an ester such as ethyl acetate or acetonitrile, if appropriate in the presence of a co-solvent such as an alkanol like methanol, ethanol, isopropanol or, preferably, terbutanol, at a temperature preferably between –10° and +10° C.

In a more preferred process, the oxidation is carried out with perphthalic acid in tetrahydrofuran.

The process of the invention does not require the isolation of any intermediate, the product resulting from the methylation reaction being directly hydrolyzed, then oxidized under conditions not previously envisaged and particularly useful from an industrial point of view. Therefore, this process does not require the passage of the intermediate enol in any stabilized form, nor final hydrolysis to isolate the product. It is believed to be the first time that the oxidation of such an enol has been directly produced.

British Patent No. 2,001,990 describes the preparation of compounds of formula I which consists of methylating an unsaturated 16 derivative, then preparing and isolating the hydroperoxide of the formula

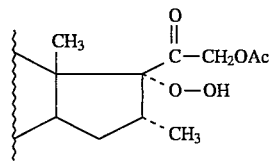

which is then reduced by zinc in acetic acid or by an alkali metal iodide in an aliphatic ketone. It is a process which, in principle as well as in the intermediates that it uses, is different from that of the present invention.

The compounds of formula II are known and described, for example, in the U.S. Pat. Nos. 2,345,711, 2,883,400, 2,963,496, 2,966,504, 2,975,197, 3,029,233, 3,210,341, 3,377,343, 3,839,369, 3,976,638, 4,031,080, 4,277,409 and 4,929,395, German Patent No. 2,207,420, Dutch Patent No. 6,902,507 or Belgian Patent No. 539,498, No. 540,478, No. 711,016, or can be easily prepared from the compounds described in these patents by processes known to one skilled in the art.

The 16α-methyl compounds of formula I are known to possess an anti-inflammatory activity and this formula includes in particular dexamethasone, its flumethasone derivatives (6α-fluoro), paramethasone derivatives (6α-fluoro 9H) and its possible precursors (Δ9,11,9-α-OH or 9,11-epoxy).

In the following examples, there are described several preferred embodiments to illustrate the invention. However, it should be understood that the invention is not intended to be limited to the specific embodiments.

EXAMPLE 1

9β,11β-epoxy-16α-methyl-21-acetyloxy-Δ1, 4-pregnadiene-17α-ol-3,20-dione 0.2 g of monohydrated cupric acetate, 7.66 g of 9β,11β-epoxy-21-acetyloxy-Δ 1,4,16(17)-pregnatriene-3,20-dione and 100 ml of anhydrous tetrahydrofuran were mixed together under an inert gas atmosphere. After 10 minutes at 20° C., the mixture was cooled to −20° C. and 8.8 ml of a 3M solution of methyl magnesium chloride in tetrahydrofuran were added over 2 hours. The mixture was stirred for 15 minutes and then the reaction mixture was cooled to −30° C. The mixture was poured slowly under an inert gas atmosphere into 80 ml of a mixture at 0° C. of phosphoric acid (1 M) and sodium hydroxide (1.35 M). The mixture was stirred and then, after 40 minutes, 1 ml of hydrogen peroxide (1 M) was added at +15° C. After one hour of stirring at +15°/+20° C., 8 g of sodium chloride were added followed by stirring for 10 minutes. After decanting under an inert gas atmosphere, the aqueous phase was extracted with tetrahydrofuran and the organic phase was washed with 10 ml of the above phosphoric acid-sodium hydroxide mixture. 2 g of sodium chloride were added and the mixture was stirred for a few minutes, then decanted. 2 g of sodium chloride were added to the organic phase and then stirring and decanting were repeated.

8 g of phthalic anhydride and 5 ml of 1M hydrogen peroxide were mixed together with stirring for one hour at ambient temperature and then 5 ml of tetrahydrofuran were added. The mixture was stirred for 75 minutes and a further 3 ml of tetrahydrofuran were added. After stirring for one hour, a further 5 ml of tetrahydrofuran were added. After stirring for one hour, a further 5 ml of tetrahydrofuran were added. The reaction mixture was stirred for another hour.

8 g of anhydrous sodium sulfate were added to the enol solution prepared above at 0°/+3° C. and under an inert gas atmosphere. The peracid suspension prepared above was added to this and after 2 hours of stirring at about +5° C., the mixture was neutralized by the addition of 9 g of sodium bicarbonate in 90 ml of water. 8 g of sodium chloride were added and the mixture was stirred for 15 minutes, followed by decanting. The aqueous phase was extracted with ethyl acetate and the combined organic phases were washed with salt water, then dried and concentrated under reduced pressure at about 30° C. to obtain 6.6 g of the crude product. 1/5th of the crude product was chromatographed on silica, eluting with a methylene chloride-ethyl ether mixture (7-3) to obtain 1.321 g of the expected product which was a yield of 80%.

IR Spectrum ($CHCl_3$)

Absorptions at 3610 $cm^{-1}$ (OH); 1747–1728 $cm^{-1}$ (C=O); 1663-1625-1607 $cm^{-1}$ (Δ1,4 3 one).

NMR Spectrum ($CDCl_3$-300 MHz-ppm)

0.88 (d): $CH_3$ in position 16; 0.93:$CH_3$ in position 18: 1.44: $CH_3$ in position 19; 2.16: $CH_3$ of —OAc; 2.94: —OH; 3.21: H in position 11; 4.69 (d) and 5.04 (d): 2H in position 21; 6.14: H in position 4; 6.20: H in position 2; 6.62: H in position 1.

EXAMPLE 2

16α-methyl-21-acetyloxy-Δ1,4,9(11)-pregnatrien-17α-ol-3,20-dione

Using the procedure of Example 1, 0.02 g of monohydrated cupric acetate and 0.733 g of 16α-methyl-21-acetyloxy-Δ 1,4,9(11),16(17)-pregnatetraene-3,20-dione in 10 ml of tetrahydrofuran were reacted. Then, 1 ml of a 3M solution of methyl magnesium chloride in tetrahydrofuran, 8 ml of a phosphoric acid-sodium hydroxide mixture and 0.1 ml of hydrogen peroxide were reacted. The peracid was prepared as in Example 1 from 0.59 g of phthalic anhydride. After purification by chromatography on silica and eluting with a methylene chloride-ethyl ether mixture (7-3), 0.4 g of the expected product were obtained.

NMR Spectrum (CDCl3-300 MHz-ppm)

0.75: $CH_3$ in position 18; 0.94 (d) : $CH_3$ in position 16; 1.40: $CH_3$ in position 19; 2.17: $CH_3$ of —OAc; 4,82 (d) −4.99 (d): 2H in position 21; 5.57: H in position 11; 6.05: H in position 4; 6,28: H in position 2; 7.19: M in position 1.

EXAMPLE 3

9α-fluoro-16α-methyl-21-acetyloxy-Δ1,4-pregnadiene-11β,17α-diol -3,20-dione

Using the procedure of Example 1, 0.02 g of monohydrated cupric acetate and 0.805 g of 9α-fluoro-21-acetyloxy-Δ1,4,9(11) -pregnatriene-11β-ol-3,20-dione in 15 ml of tetrahydrofuran were reacted. Then, 2 ml of a 3M solution of methyl magnesium chloride in tetrahydrofuran, 12 ml of a phosphoric acid-sodium hydroxide mixture and 0.1 ml of hydrogen peroxide were reacted. The peracid was prepared as in Example 1 from 0.59 g of phthalic anhydride. After purification by chromatography on silica, eluting with a methylene chloride-ethyl acetate mixture (7-3), 0.25 g of the expected product were obtained.

NMR Spectrum (CDCl3-300 MHz-ppm)

0.93 (d): $CH_3$ in position 16; 1.07: $CH_3$ in position 18; 1.57: $CH_3$ in position 19; 2.17: $CH_3$ of —OAc; 3.39:OH in position 11-beta and 17-alpha; 4.38: H in position 11; 4.92: 2H in position 21; 6.11: H in position 4; 6.33: H in position 2; 7.25: H in position 1.

EXAMPLE 4

9β-fluoro-11β-21-diacetyloxy-16α-methyl-Δ1,4-pregnadiene-17α-ol -3,20-dione

Using the procedure of Example 1, 0.02 g of monohydrated cupric acetate and 0.889 g of 9α-fluoro-11β, 21-diacetyloxy -Δ1,4,9(11)-pregnatriene-17α-ol-3,20-dione in 10 ml of tetrahydrofuran were reacted. Then, 1 ml of a 3M solution of methyl magnesium chloride in tetrahydrofuran, 8 ml of a phosphoric acid-sodium hydroxide mixture and 0.1 ml of hydrogen peroxide were reacted. The peracid was prepared as in Example 1 from 0.59 g of phthalic anhydride. After purification by chromatography on silica, eluting with a methylene chloride-ethyl ether mixture (7 -3), 0.634 g of the expected product were obtained.

NMR Spectrum (CDCl3-300 MHz-ppm)

0.93 (d): $CH_3$ in position 16; 0.93: $CH_3$ in position 18; 1.58: $CH_3$ in position 19; 2.13–2.15: $CH_3$ of —OAc in position 21 and 11-beta; 2.74: OH; 4.71 (d) −4,99 (d): 2H in position 21; 5.42 (m): H in position 11-alpha; 6.11: H in position 4; 6.33: H in position 2: 6.82: H in position 1.

EXAMPLE 5

9β, 11β-epoxy-16α-methyl-Δ1,4-pregnadiene-17α-ol-3,20-dione

Using the procedure of Example 1, 0.02 g of monohydrated cupric acetate and 0.649 g of 9β, 11β-epoxy-Δ1,4, 16(17) -pregnatriene-3,20-dione in 10 ml of tetrahydrofuran were reacted. Then, 0.9 ml of a 3M solution of methyl magnesium chloride in tetrahydro- furan, 8 ml of a phosphoric acid sodium hydroxide and 0.1 ml of hydrogen peroxide were reacted. The peracid was prepared as in Example 1 from 0.59 g of phthalic anhydride. After purification by chromatography on silica, eluting with a methylene chloride-ethyl-ether mixture (7-3), 0.234 g of the expected product were obtained.

NMR Spectrum (CDCl3-300 MHz-ppm)

0.88 (d): $CH_3$ in position 16; 1.01: $CH_3$ in position 18; 1.44: $CH_3$ in position 19; 2.24: $CH_3$ in position 21; 3.05: OH in position 17; 3.21: H in position 11-alpha; 6.15: H in position 4; 6.18: H in position 2; 6.60: H in position 1.

EXAMPLE 6

9β, 11β-epoxy-16α-methyl-21-acetyloxy-Δ1,4-pregnadiene-17α-ol-3,20-dione 3.06 g of 9β, 11β-epoxy-21-acetyloxy-Δ1,4,16(17)-pregnatriene-3,20-dione and 0.08 g of monohydrated cupric acetate in 33 ml of tetrahydrofuran were mixed together under an inert gas atmosphere and after the mixture was cooled, 4 ml of a 3M solution of methyl magnesium chloride in tetrahydrofuran were introduced at −20° C. over one hour. The mixture was stirred for one hour and then the reaction mixture was cooled to −30° C. The mixture was poured slowly into 30 ml of a phosphoric acid and sodium hydroxide mixture (1M/1.35M) cooled to 0° C. The mixture was allowed to reheat with stirring and, then 0.4 ml of 1M hydrogen peroxide was added at +15° C. After one hour at +15, +20° C., 4 g of sodium chloride were added and the mixture was stirred for 10 minutes, followed by decanting under an inert gas atmosphere. The aqueous phase was extracted with tetrahydrofuran and then the organic phase was washed with 5 ml of the above phosphoric acid-sodium hydroxide mixture. 1 g of sodium chloride was added and then the water was decanted and the mixture was made up to 50 ml. 10 ml of solution were removed under an inert gas atmosphere, followed by concentrating to dryness, then taking up in methylene chloride. After cooling to 0° C., 0.1 ml of hexachloroacetone, then 0.6 ml of 1M hydrogen peroxide were added. The mixture was stirred at 0°, +5° C. for 15 hours and then a small amount of water saturated with sodium chloride was added. The organic phase was decanted, dried and concentrated to dryness. The residue was chromatographed on silica, eluting with a methylene chloride-ethyl ether mixture (7 -3) to obtain 0.047 g of the expected product.

NMR Spectrum (CDCl3-300 MHz-ppm)

0.88 (d): $CH_3$ in position 16; 0.93: $CH_3$ in position 18; 1.44: $CH_3$ in position 19; 2.16: $CH_3$ of —OAc; 2.94: OH; 3.21: H in position 11-alpha; 4.69 (d) −5.04 (d): 2H in position 21; 6.14: H in position 4; 5.20: H in position 2; 6.62: H in position 1.

EXAMPLE 7

9β, 11β-epoxy-16α-methyl-21-acetyloxy-Δ1,4-pregnadiene-17α-ol-3,2-dione

Using the procedure of Example 6 up to the removal under an inert gas atmosphere of 10 ml of solution resulting from the hydrolysis, concentration to dryness was carried out, followed by taking up in methylene chloride. A mixture of 4 g of potassium permaganate, 2 g of copper sulfate ($5H_2O$) and 0.2 ml of water was added and then 1 ml of terbutyl alcohol was added. The mixture was stirred for 3 hours at 20° C., followed by filtering, drying and concentrating to dryness. The residue was chromatographed on silica, eluting with cyclohexane-ethyl acetate (1—1), then methylene chloride-ethyl ether (7-3) mixture to obtain 0.072 g of the expected product.

NMR Spectrum (CDCl3-300 MHz-ppm)

0.88 (4): $CH_3$ in position 16; 0.93: $CH_3$ in position 18; 1.44: $CH_3$ in position 19; 2.16: $CH_3$ of —OAc; 2.94: OH; 3.21: H in position 11-alpha; 4.69 (d) −5.04 (d): 2H in position 21; 6.14: H in position 4; 6.20: H in position 2; 5.62: H in position 1.

Various modifications of the process of the invention may be made without departing from the spirit or scope thereof and it is to be understood that the invention is intended to be limited only as defined in the appended claims.

What is claimed is:

1. A process for the preparation of a compound of the formula

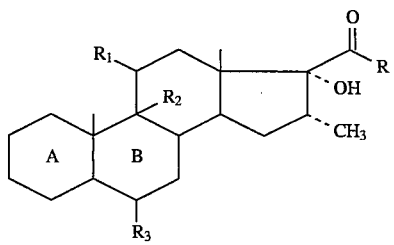

in which rings A and B are a remainder:

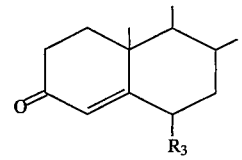

in which the 3-ketone function is optionally protected in the form of a ketal, thioketal, hemithioketal or enol ether, or a remainder:

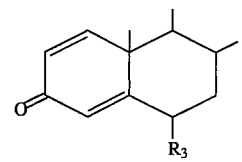

wherein R is methyl or —$CH_2$—OR', R' is hydrogen or ether remainder or ester remainder, $R_1$ and $R_2$ together form a second bond, or $R_1$ and $R_2$ form together an epoxide in beta position, or $R_1$ is hydrogen, ketone or α- or β- hydroxy, free or protected in the form of an ether or ester and $R_2$ is hydrogen, or $R_1$ is hydrogen and $R_2$ is α-hydroxy function, or $R_1$ is β-hydroxy, free or protected in the form of an ether or ester and $R_2$ is α-fluorine or bromine and $R_3$ is hydrogen or α or β fluorine or methyl consisting essentially of reacting a compound of the formula

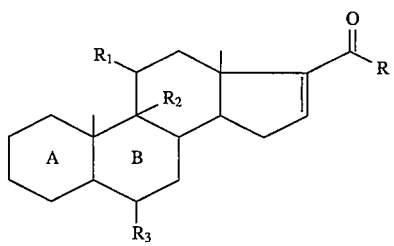

in which A, B, R, $R_1$, $R_2$ and $R_3$ have the above meaning with a methylation agent in the presence of a copper-based catalyst to form the 16α-methylated enolate, hydrolyzing the latter to obtain the corresponding enol and reacting the latter with an oxidizing agent to obtain the compound of formula I.

2. The process of claim 1 wherein A and B are

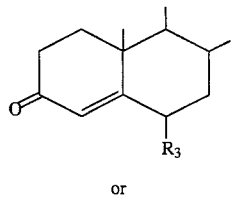

or

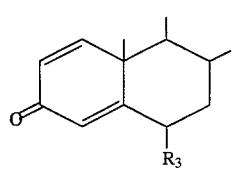

in which $R_3$ is defined as in claim 1 and the 3-ketone function is free.

3. The process of claim 1 wherein $R_1$ and $R_2$ together from a second bond, or $R_1$ and $R_2$ form a β-epoxide, or $R_1$ is β-hydroxy, free or protected in the form of an ether or ester and $R_2$ is α-fluorine and $R_3$ is hydrogen, fluorine or methyl.

4. The process of claim 1 wherein rings A and B are

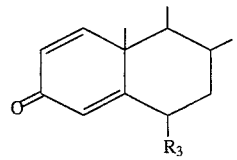

5. The process of claim 1 wherein the methylation agent is a methylated derivative of copper or methyl magnesium chloride, bromide or iodide used in the presence of a copper-based catalyst.

6. The process of claim 1 wherein the methylation agent is methyl magnesium chloride, bromide or iodide in the presence of cupric acetate or propionate.

7. The process of claim 1 wherein the hydrolysis agent is selected from the group consisting of a monoalkali metal phosphate, ammonium chloride, ammonium acetate, a weak acid and a buffer of weakly acidic pH.

8. The process of claim 1 wherein the hydrolysis is followed by an oxidizing treatment of the cupric ions present in the mixture.

9. The process of claim 1 wherein the oxidizing agent for the enol is selected from the group consisting of peracids, hydrogen peroxide, dioxiranes, hydroperoxides and potassium permanganate.

10. The process of claim 9 wherein the oxidizing agent is a peracid.

11. The process of claim 1 wherein the oxidation is carried out in a halogenated solvent or an ether or an aromatic solvent, an ester or acetonitrile is used in the presence of a cosolvent.

12. The process of claim 1 wherein the oxidation is carried out with perphthalic acid in tetrahydrofuran.

* * * * *